(12) United States Patent
Mendel-Hartvig et al.

(10) Patent No.: US 6,777,198 B2
(45) Date of Patent: Aug. 17, 2004

(54) ASSAY METHOD AND KIT THEREFOR

(75) Inventors: Ib Mendel-Hartvig, Uppsala (SE); Lena Odelstad, Uppsala (SE)

(73) Assignee: Pharmacia Diagnostics AB, Uppsala (SE)

( * ) Notice: Subject to any disclaimer, the term of this patent is extended or adjusted under 35 U.S.C. 154(b) by 0 days.

(21) Appl. No.: 09/972,882

(22) Filed: Oct. 10, 2001

(65) Prior Publication Data

US 2002/0061600 A1 May 23, 2002

Related U.S. Application Data

(60) Provisional application No. 60/241,366, filed on Oct. 19, 2000.

(30) Foreign Application Priority Data

Oct. 11, 2000 (SE) .............................................. 0003662

(51) Int. Cl.⁷ ........................ G01N 33/53; G01N 33/543
(52) U.S. Cl. ..................... 435/7.94; 435/7.1; 435/7.92; 435/971; 436/518; 436/524
(58) Field of Search ................................ 435/7.1, 7.92, 435/7.94, 7.5, 971, 800, 805; 436/518, 501, 524, 532

(56) References Cited

U.S. PATENT DOCUMENTS

| | | | |
|---|---|---|---|
| 4,373,932 A | | 2/1983 | Gribnau et al. |
| 4,623,461 A | * | 11/1986 | Hossom et al. ............. 210/445 |
| 4,693,969 A | | 9/1987 | Saxena et al. |
| 5,063,081 A | | 11/1991 | Cozzette et al. |
| 5,187,065 A | | 2/1993 | Schutzer |
| 5,296,347 A | * | 3/1994 | LaMotte, III, et al. ........... 435/5 |
| 5,420,016 A | * | 5/1995 | Boguslaski et al. ........... 435/12 |
| 5,569,608 A | * | 10/1996 | Sommer et al. ............ 436/518 |
| 5,573,909 A | * | 11/1996 | Singer et al. ................... 435/6 |
| 6,183,972 B1 | * | 2/2001 | Kuo et al. .................... 435/7.1 |
| 6,184,042 B1 | * | 2/2001 | Neumann et al. .......... 435/7.94 |
| 6,316,205 B1 | * | 11/2001 | Guan et al. .................. 435/7.1 |
| 6,319,676 B1 | * | 11/2001 | Nazareth et al. ............. 435/7.5 |

FOREIGN PATENT DOCUMENTS

| | | | | |
|---|---|---|---|---|
| EP | 0 378 391 A2 | | 7/1990 | |
| EP | 0 617 287 A2 | | 9/1994 | |
| GB | 0105714 | * | 4/1984 | .......... G01N/33/54 |
| JP | 58211659 A | | 9/1983 | |
| JP | 611498863 A | | 7/1986 | |
| WO | 98/18968 | | 5/1998 | |

OTHER PUBLICATIONS

Bayer et al (The Avidin–Biotin System, Immunoassay, Chapter 11, pp. 237–267, edited by Eleftherious P. Diamandis, 1996).*
Maggio et al (Enzyme–Immunoassay, p. 186–187, 1987).*
Seiichi Hashida et al., Biotechnology Annual Review, vol. 1, pp. 403–451.
John E. Butler, Journal of Immunoassay, vol. 21(2&3), pp. 165–209, (2000).
Eiji Ishikawa et al., Molecular and Cellular Probes, vol. 5, pp. 81–95, (1991).
John E. Butler, Methods, vol. 22, pp. 4–23, (2000).
Gert Doekes, Occupational and Environmental Medicine, vol. 53, pp. 63–70, (1996).

* cited by examiner

*Primary Examiner*—Long Le
*Assistant Examiner*—Gary W. Counts
(74) *Attorney, Agent, or Firm*—Dinsmore & Shohl LLP

(57) ABSTRACT

The invention relates to a method of determining an analyte in a sample, especially a high concentration analyte, comprises the steps of:

a) contacting the sample with a specified amount of a receptor which binds specifically to the analyte to form an analyte/receptor complex, said specified amount of receptor being in excess of that required to bind all analyte in the sample, b) isolating on a solid phase a specified fraction of the amount of receptor contacted with the analyte, including analyte/receptor complex and unreacted receptor, c) detecting the amount of analyte/receptor complex in said isolated specified fraction, and d) from the detected amount analyte/receptor complex, determining the concentration of analyte in the sample.

The invention also relates to test kits for carrying out the method.

21 Claims, No Drawings

ASSAY METHOD AND KIT THEREFOR

This application claims benefit of provisional application serial No. 60/241,366 Oct. 19, 2000.

FIELD OF THE INVENTION

The present invention relates to a method of quantitatively or semi-quantitatively determining an analyte in a sample, especially a high concentration analyte.

BACKGROUND OF THE INVENTION

For qualitative and quantitative determination of an analyte in a sample, a so-called sandwich assay is often used, wherein two receptors directed against different epitopes of the analyte are incubated with a sample containing the analyte, one of the receptors being detectable, e.g. through a label conjugated thereto. In a heterogeneous assay format, the second receptor is immobilized (e.g. coupled) to a solid phase or provided with a binder component, such as biotin, capable of binding to the solid phase, such as an avidin- or streptavidin-coated solid phase.

Especially in case the analyte is present in the sample in a high concentration, it is customary to dilute the sample before performing the assay to avoid the use of large and often costly amounts of immobilized receptor and labelled receptor, respectively, or to avoid technical difficulties where large amounts of receptors cannot be used. Such dilution is not only laborious but also introduces an additional source of error into the assay.

There is therefore a need of an assay procedure that avoids the necessity of dilution.

SUMMARY OF THE INVENTION

It is an object of the present invention to provide a method of performing a heterogeneous sandwich assay which permits the determination of even a high concentration analyte in a sample without the need to dilute the sample.

It is another object of the invention to provide a method of performing a heterogeneous sandwich assay which reduces the amounts of capturing and detection reagents used.

It is still another object of the invention to provide test kits for carrying out the method.

In one aspect of the present invention there is therefore provided a method of determining an analyte in a sample, especially a high concentration analyte found in concentrations>1 nmole/liter, comprising the steps of:
  a) contacting the sample with a specified amount of a receptor which binds specifically to the analyte to form an analyte/receptor complex, said specified amount of receptor being in excess of that required to bind all analyte in the sample,
  b) isolating on a solid phase, preferably a matrix such as a membrane strip, a specified fraction of the amount of receptor contacted with the analyte, including analyte/receptor complex and unreacted receptor,
  c) detecting the amount of analyte/receptor complex in said isolated specified fraction, and
  d) from the detected amount analyte/receptor complex, determining the concentration of analyte in the sample.

In another aspect of the present invention there is provided a test kit for determining an analyte in a sample, comprising (i) a specified amount of a receptor substance having a first part which binds specifically to the analyte, and (ii) a solid phase member having immobilized thereon a ligand which binds specifically to a second part of the receptor, the amount of said ligand on the solid phase member being less than said specified amount of the receptor substance.

In still another aspect of the present invention there is provided a test kit for determining an analyte in a sample, comprising (i) a specified amount of a receptor substance having a first part which binds specifically to the analyte, only a specified fraction of the amount of receptor substance having a second part capable of binding to a specific ligand, and (ii) a solid phase member having said specific ligand immobilized thereon.

In yet another aspect of the present invention there is provided a test kit for determining an analyte in a sample, comprising (i) a first specified amount of a receptor substance, and (ii) a solid phase member having immobilized thereon a second specified amount of the receptor substance.

While it is preferred to use the method and test kit for quantitative determination of analytes of interest, they may also be used for semi-quantitative and qualitative determinations.

DETAILED DESCRIPTION OF THE INVENTION

The essence of the present invention resides in binding all analyte present in a sample to an analyte-specific receptor, isolating a minor fraction of the analyte-receptor complex formed on a solid phase, detecting the amount of isolated analyte-receptor complex, and from this detected amount of analyte on the solid phase determining the total amount of analyte in the sample. According to the invention, this may be accomplished in various ways.

In one embodiment of method of the invention, all analyte is bound by contacting the analyte-containing sample with a solution containing an excess of a first receptor (R1) which in addition to affinity to the analyte has affinity to a ligand (L), whereupon a minor fraction of the analyte-receptor complex is bound to a solid phase having the ligand (L) immobilized thereto. This binding of the minor fraction may be achieved by either (i) using a limited (specified) amount of ligand (L) to extract a fraction of the analyte-receptor complex (and unreacted receptor), or (ii) by using a first receptor (R1) only a minor (specified) fraction of which is capable of binding to the ligand (L) to extract the desired fraction of the analyte-receptor complex (and unreacted receptor). In the latter case (ii), the amount of immobilized ligand (L) is usually in excess of the amount of the first receptor capable of binding to the ligand (L). The amount of analyte/receptor complex bound to the solid phase is then detected, usually by contacting the solid phase with a detecting agent in the form of a labelled binder for the analyte, such as a labelled second receptor (R2).

In the first case (i) above, the amount of immobilized ligand (L) that can bind to the analyte-specific receptor (R1) is a specified fraction of the amount of analyte-specific receptor (R1) contacted with the sample, and therefore the ratio of detected analyte on the solid phase to the total amount of analyte in the sample will correspond to the ratio of immobilized analyte-binding ligand (L) to the total amount of added receptor (R1), thereby permitting the analyte concentration in the sample to be calculated.

In the second case (ii) above, the amount of analyte-specific receptor (R1) that can bind to immobilized ligand (L) is a specified fraction of the total amount of receptor (R1), and therefore the ratio of detected analyte on the solid phase to the total amount of analyte in the sample will correspond to the ratio of analyte-specific receptor (R1) capable of reacting with ligand (L) to the total amount of receptor (R1), thereby permitting the analyte concentration in the sample to be calculated.

The term "receptor" as used herein refers to active analyte-binding receptor, and, where relevant, active ligand-binding receptor, respectively, and is not meant to include such receptor in an inactive or non-binding state. Likewise, the term receptor-binding ligand refers to active receptor-binding ligand and is not meant to include such ligand in an inactive or non-binding state.

The term "amount" as used herein usually means binding capacity. Thus, for example, when it is stated that the amount of analyte-specific receptor is in excess of the amount of analyte, it means that there is more analyte-specific receptor than necessary to bind all analyte. Usually, there is a 1:1 reaction ratio between e.g. the analyte and the analyte-specific receptor, or between the analyte specific receptor and the immobilized receptor-binding ligand. In such a case, the binding capacities of the respective species correspond to their molar amounts. Other reaction ratios are, however, also possible. For example, the immobilized ligand may be capable of binding more than one analyte-specific receptor.

In another embodiment of method of the invention, the sample is contacted with analyte-specific receptor (R1) provided both in solution and, in a minor fraction, immobilized to a solid phase, thereby permitting a minor fraction of analyte present in the sample to be bound to the solid phase. If the ratio of the amount of receptor (R1) in solution to the amount of immobilized receptor (R1) is known, the analyte concentration in the sample may be calculated from the detected amount of analyte bound to the solid phase.

It is readily seen that the above procedure gives the same effect as diluting the sample. In addition to the dilution step being avoided, which, of course, is of advantage to the operator, one obtains a considerable saving in reagents, i.e. both the reagent for capturing the analyte on the solid phase and the detecting agent, the latter often being costly. In this connection, it is also to be noted that in the assay of the invention, the reaction between analyte and receptor takes place in solution where almost all receptors are active rather than at a solid phase surface as in a corresponding conventional assay where only about 10–20% of immobilized receptor will react (Butler, J. E., et al, Molecular Immunology, Vol. 30, No. 13, pp. 1165–1175, 1993).

The required ratio between the total binding capacity of analyte-specific receptor contacted with the sample and (i) the binding capacity of receptor-binding ligand that is immobilized to the solid phase when this is limited, or (ii) the ligand-binding capacity of the analyte-specific receptor when this is limited, is readily determined by the skilled person depending inter alia on the particular analyte to be determined and the particular assay format used and may be chosen within wide limits. Usually, this ratio is from about 2:1 to about 1000:1, especially from about 5:1 to about 100:1, preferably more than about 10:1, more preferably more than about 20:1.

The excess of analyte receptor relative to the amount of analyte in the sample is also readily determined by the skilled person for each specific case.

The receptor contacted with the sample is usually of the dual receptor or bireactive binder type having one part that specifically binds to the analyte and another part which specifically binds to the ligand immobilized on the solid phase surface. The analyte binding part may, for example, be an antibody (monoclonal or polyclonal) or an active fragment thereof (including recombinant antibodies and fragments) or nucleic acids whereas the ligand-binding part may be one member of a specific binding pair. Exemplary such specific binding pairs include immunological binding pairs, such as antigen-antibody and hapten-antibody, biotin-avidin or -streptavidin, lectin-sugar, hormone-hormone receptor, and nucleic acid duplex. For example, the solid phase may have streptavidin immobilized thereto, and the receptor for the analyte may be biotinylated. To avoid immunoprecipitation at high analyte concentrations, it may be preferable to use monovalent receptors.

While the analyte preferably is a molecule present in concentrations>1 nmole/liter in a sample, the analyte may, of course, be any substance for which there exists a naturally occurring analyte-specific binding member or for which an analyte-specific binding member can be prepared.

Analyte that has been captured by the solid phase is usually detected by reaction with a labelled specific binder for the analyte. Such a labelled binder may be a conjugate comprising a detectable label covalently or non-covalently attached to the specific binding member, "label" referring to any substance which is capable of producing a signal that is detectable by visual or instrumental means, particularly a fluorophore or chromophore.

The sample is usually of biological origin, for example blood (serum, plasma, whole blood), saliva, tear fluid, urine, cerebrospinal fluid, sweat, etc. The invention is, of course, also applicable to other types of samples, such as fermentation solutions, reaction mixtures, etc. Especially, however, the sample is an undiluted serum or whole blood sample.

While the present invention is generally applicable, it may advantageously be used in solid phase assays of the immunochromatograpic type. Such assays use a device comprising a plate-shaped flow matrix of bibulous material, usually a membrane strip, such as of cellulose nitrate or glass fiber, in which liquid can be transported laterally (i.e. in the plane of the strip) by capillary forces in the membrane. The membrane usually has a sample application zone, and a detection (or reaction) zone downstream of the sample application zone. In the detection zone, usually a capturing reagent for the analyte is immobilized. To conduct an assay, the application zone is contacted with the liquid sample to be assayed for the analyte of interest. The device is maintained under conditions sufficient to allow capillary action of liquid to transport the analyte of interest, if present in the sample, through the membrane strip to the detection zone where the analyte is captured. The capillary liquid flow is usually insured by an absorbing pad or the like at the downstream end of the strip. A detection reagent, usually labelled, is then added upstream of the detection zone and interacts with captured analyte in the detection zone, and the amount of captured analyte is measured. Often, the detection reagent is pre-deposited in or on the membrane strip, e.g. in the form of diffusively movable particles containing fluorophoric or chromogenic groups, either upstream of the sample application zone or between the sample application zone and the detection zone.

In an immunochromatographic assay according to the invention, the receptor is added to the sample either before applying the sample to the membrane strip, or may be pre-deposited in or on the membrane strip upstream of the detection zone.

A test kit for carrying out the method of the invention may comprise such a membrane having (i) immobilized in or on the membrane a ligand which binds specifically to the receptor, and (ii) dissolvably pre-deposited in or on the membrane a specified amount of analyte-specific receptor. The amount of the ligand on the solid phase member is less, and usually considerably less than that required to bind the specified amount of the receptor substance.

In another embodiment of test kit, only a fraction of the analyte-specific receptor is capable of binding to the immobilized ligand. Such a kit may comprise (i) immobilized in or on a membrane a ligand which binds specifically to the receptor, and (ii) dissolvably pre-deposited in or on the membrane a specified amount of analyte-specific receptor substance, only a specified fraction of which is capable of binding to the immobilized ligand.

Still another embodiment of test kit may comprise (i) dissolvably pre-deposited in or on a membrane a first specified amount of analyte-specific receptor substance, and (ii) immobilized in or on the membrane a second specified amount of the analyte-specific receptor substance.

In an alternative embodiment, the solid phase is a solid phase well, such as a microtiter plate well. Such of test kit may comprise a solid support having one or more wells with the second amount of analyte binding receptor immobilized therein and with the first amount of analyte-binding receptor dissolvably pre-deposited in the well or in close contact with the well.

In the following, the invention will be illustrated in more detail by a specific non-limiting Example.

EXAMPLE 1

Immunoassay for C-reactive Protein (CRP) in Undiluted Serum Samples Measuring Range 10–200 mg/l Principle Sample is mixed with biotinylated anti-CRP-fab in excess and the mixture is applied to a test strip having a deficient amount of streptavidin in the reaction zone. After an intermediate wash, anti-CRP fluorophore-conjugate is added and after a wash, conjugate that has bound to the reaction zone is measured. Since only a small part of the biotinylated anti-CRP-fab can bind to the reaction zone the consumption of the fluorophore conjugate is reduced considerably.

Test Strips

5×48 mm nitrocellulose membranes (Whatman, porosity 8 μm) on a polyester backing were used. The strips had a sample application zone at one end and a downstream reaction zone with immobilized streptavidin in an amount capable of binding approximately 6% of biotinylated anti-CRP added in the assay procedure.

Samples

CRP-containing samples of varying CRP concentration were prepared from a 200 mg/l of recombinant CRP (Fitzgerald) in hCRP depleted serum.

Procedure

15 μl of biotinylated anti-CRP-fab (monovalent fab-fragment of monoclonal antibody) and 15 μl of CRP-containing serum were mixed and the mixture was applied to the application zone of the membrane strip. The amount of biotinylated anti-CRP-fab was 3 μg per test strip, which is a 2× molar excess of anti-CRP in relation to the standard 200 mg/l CRP. After an intermediate wash with 15 μl of test buffer (50 mM borate buffer pH 8.0, 3% BSA, 5% sucrose, 0.15 M NaCl, 0.005% CaCl$_2$, 0.05% NaN$_3$), 15 μl of detection conjugate solution [3 μg of anti-CRP monoclonal antibody (Fitzgerald) coupled to 0.1 μm TransFluoSpheres-SO$_4$/CHO (633/720 nm) (Molecular Probes Inc.), the above test buffer] were added, followed by wash with 2×15 μl of test buffer. The fluorescence of the strip was then measured. The results are shown in Table 1 below.

TABLE 1

| CRP conc. (mg/l) | Peak area obtained (V × mm) |
|---|---|
| 0 | 0.08 |
| 0 | 0.07 |
| 10 | 2.56 |
| 10 | 2.50 |
| 30 | 3.62 |
| 30 | 4.01 |
| 100 | 5.24 |
| 100 | 4.87 |
| 200 | 6.28 |
| 200 | 5.82 |

EXAMPLE 2 (COMPARATIVE)

Immunoassay for CRP in Serum Samples Diluted 1/20 Measurement Range 10–200 mg/ml Principle Sample is diluted in test buffer and applied to test strips having an excess of anti-CRP in the reaction zone. Anti-CRP fluorophore-conjugate is then added followed by a wash, whereupon conjugate that has bound to the reaction zone is measured. Sample dilution is necessary to avoid unreasonably large amounts of anti-CRP in the reaction zone as well as in the detection conjugate.

Test Strips

5×48 mm nitrocellulose membranes (Whatman, porosity 8 μm) on a polyester backing were used. The strips had a sample application zone at one end and a downstream reaction zone with 2.6 μg immobilized anti-CRP monoclonal antibody (Fitzgerald), which is a 13× molar excess in relation to a standard 10 mg/ml CRP serum.

Samples

CRP-containing samples of varying CRP concentration were prepared from a 200 mg/l of recombinant CRP (Fitzgerald) in hCRP depleted serum.

Procedure

15 μl of CRP-containing serum diluted 1/20 in test buffer (50 MM borate buffer pH 8.0, 3% BSA, 5% sucrose, 0.15 M NaCl, 0.005% CaCl$_2$, 0.05% NaN$_3$) were applied to the application zone of the membrane strip. Then, 15 μl of detection conjugate solution [anti-CRP monoclonal antibody (Fitzgerald) coupled to 0.1 μm TransFluoSpheres-SO$_4$/CHO (633/720 nm) (Molecular Probes Inc.), the above test buffer] were added, the amount of anti-CRP conjugate being 3 μg per test strip which was a 1533 molar excess in relation to the highest standard value. The conjugate addition was followed by a wash with 15 μl The fluorescence of the strip was then measured. The results are shown in Table 2 below.

TABLE 2

| CRP conc. (mg/l) | Peak area obtained (V × mm) |
|---|---|
| 0 | 0.41 |
| 0 | 0.60 |
| 10 | 7.51 |
| 10 | 7.130 |
| 20 | 8.86 |
| 20 | 9.42 |
| 40 | 11.97 |
| 40 | 10.67 |

TABLE 2-continued

| CRP conc. (mg/l) | Peak area obtained (V × mm) |
|---|---|
| 80 | 11.70 |
| 80 | 12.91 |
| 200 | 14.27 |
| 200 | 14.16 |

The above Examples 1 and 2 thus demonstrate that it is possible to run an assay on undiluted high concentration samples without using huge amounts of reagents when using the methodology of the present invention.

What is claimed is:

1. A method of determining the presence of an analyte in a sample comprising the steps of:
   a) contacting the sample with a known amount of a receptor which binds specifically to the analyte to form an analyte/receptor complex, wherein the known amount of receptor is in excess of an amount of the receptor required to bind all analyte in the sample,
   b) isolating on a solid phase a fraction of the receptor contacted with the analyte, the resulting isolated fraction of receptor contacted with analyte including the analyte/receptor complex and unreacted receptor, and the ratio between the receptor in said isolated fraction and the known amount of receptor contacted with the sample being in a range of from about 1:2 to about 1:1000,
   c) labeling the analyte/receptor complex in said isolated fraction and detecting the amount of labeled analyte/receptor complex in said isolated fraction; and
   d) from the detected amount of labeled analyte/receptor complex, determining the presence of analyte in the sample.

2. The method according to claim 1 in which the sample has a concentration of greater than 1 nmole/litre.

3. The method according to claim 1 or claim 2 in which the sample is undiluted.

4. The method according to claim 1 or 2, wherein isolating said fraction of receptor contacted with the sample on the solid phase comprises providing a solid phase having binding sites incorporated thereon for the receptor, and after contacting the sample, or an aliquot thereof, with a liquid phase containing the receptor, binding said fraction of receptor to the solid phase.

5. The method according to claim 4, wherein all of the receptor contacted with the sample has reactivity towards said binding sites on the solid phase, and receptor-binding capacity of the solid phase is less than solid-phase binding capacity of receptor contacted with the sample.

6. The method according to claim 4, wherein only the ratio between the total binding capacity of receptor and binding capacity of receptor towards said binding sites on the solid phase is in the range of from about 2:1 to 1000:1.

7. The method according to claim 1 or 2, wherein isolating said fraction of receptor on the solid phase comprises contacting the resulting receptor contacted with analyte with the solid phase.

8. The method according to claim 1, wherein the receptor comprises a first part that binds specifically to the analyte, and a second part that binds to the solid phase.

9. The method according to claim 8, wherein the solid phase binding part of the receptor comprises one member of a specific binding pair, and the other member of the binding pair is immobilized to the solid phase.

10. The method according to claim 1, wherein in step c) the analyte/receptor complex is detected by a labeled detection reagent which binds specifically to the analyte.

11. The method according to claim 1, wherein said solid phase binding sites for the receptor are immobilized in a reaction zone of a flow matrix.

12. The method according to claim 1, wherein the receptor is an antibody or immunoreactive fragment thereof.

13. The method according to claim 10, wherein the detection reagent is an antibody or immunoreactive fragment thereof.

14. The method according to claim 10, wherein the detection reagent is labelled by a fluorophore or chromophore.

15. The method according to claim 9, wherein the specific binding pair is biotin-avidin or biotin-strepavidin.

16. The method according to claim 1, wherein the sample is an undiluted serum sample.

17. The method according to claim 1, wherein the sample is an undiluted whole blood sample.

18. The method according to claim 9, wherein the ratio between receptor in said isolated fraction and the known amount of receptor contacted with the sample is in a range of from about 1:5 to 1:100.

19. The method according to claim 9, wherein the ratio between receptor in said isolated fraction and the known amount of receptor contacted with the sample is no more than about 1:20.

20. The method according to claim 11, wherein said flow matrix is a lateral flow matrix.

21. The method according to claim 20, wherein said lateral flow matrix is a membrane strip.

* * * * *